United States Patent [19]
Peskin et al.

[11] Patent Number: 6,126,968
[45] Date of Patent: *Oct. 3, 2000

[54] STABLE COMPOSITIONS CONTAINING N-PROPARGYL-1-AMINOINDAN

[75] Inventors: Tirtsah Berger Peskin, Raanana; Fanny Caciularu, Tikva, both of Israel

[73] Assignee: Teva Pharmaceutical Industries, Ltd., Jerusalem, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 09/043,475

[22] PCT Filed: Sep. 18, 1996

[86] PCT No.: PCT/IL96/00115

§ 371 Date: Feb. 22, 1999

§ 102(e) Date: Feb. 22, 1999

[87] PCT Pub. No.: WO97/12583

PCT Pub. Date: Apr. 10, 1997

[30] Foreign Application Priority Data

Sep. 20, 1995 [IL] Israel ......................................... 115357

[51] Int. Cl.[7] ........................... A61K 9/46; A61K 31/135

[52] U.S. Cl. ........................... 424/466; 424/465; 514/647
[58] Field of Search ............................ 514/647; 424/465, 424/466

[56] References Cited

U.S. PATENT DOCUMENTS

| | | | |
|---|---|---|---|
| 3,513,244 | 5/1970 | Gittos et al. | 424/320 |
| 5,137,730 | 8/1992 | Dennis et al. | 424/465 |
| 5,225,197 | 7/1993 | Bolt et al. | 424/440 |
| 5,387,612 | 2/1995 | Youdim et al. | 514/647 |
| 5,792,473 | 8/1998 | Gergely et al. | 424/466 |

FOREIGN PATENT DOCUMENTS

| | | |
|---|---|---|
| 201730 | 3/1988 | Hungary . |
| 204504 | 5/1990 | Hungary . |
| WO9626720 | 9/1996 | WIPO ................................... 514/647 |

*Primary Examiner*—James H. Reamer
*Attorney, Agent, or Firm*—John P. White; Cooper & Dunham LLP

[57] ABSTRACT

A pharmaceutical composition comprising as active ingredient a racemic, S(–), and R(+)-N-propargyl-1-aminoindan or a pharmaceutically acceptable salt thereof, and at least 60% by weight of at least one pentahydric or hexahydric alcohol. Optionally the composition may contain citric acid and magnesium stearate.

26 Claims, No Drawings

STABLE COMPOSITIONS CONTAINING N-PROPARGYL-1-AMINOINDAN

FIELD OF THE INVENTION

The present invention concerns formulations of racemic, S(−) or R(+) enantiomers of N-propargyl-1-aminoindan, and especially formulations of the enantiomer R(+) of N-propargyl-1-aminoindan (referred to hereinafter as R(+) PAI) which is a selective irreversible inhibitor of the B-form of the enzyme monoamine oxidase used, for example, for the treatment of Parkinson's disease. In the following the enzyme monoamine oxidase will be referred to as MAO and the B-form thereof as MAO-B.

BACKGROUND OF THE INVENTION

GB 1 003 686 discloses a group of benzocycloalkane compounds in which the cycloalkane has from five to seven ring members and is substituted by an N-(alkynylalkyl) amino group, and their use as MAO inhibitors. The patent further discloses the use of the subject compounds in admixture with a variety of substances including various alcohols such as a benzyl alcohol, stearyl alcohol, and methanol. The patent, however, does not teach how and by what criteria any of the many possible carriers and other ingredients are selected so as to overcome the stability problem of the product.

The object of the present invention is to provide stable formulations comprising an effective amount of racemic, S(−) or R(+)-N-propargyl-1-aminoindan. For the sake of simplicity, the abbreviation PAI, unless specified otherwise, will be used to denote the enantiomers of N-propargyl-1-aminoindan, as well as their racemic mixtures.

SUMMARY OF THE INVENTION

In accordance with the invention it was surprisingly found that the stability of formulations comprising PAI can be significantly improved by the incorporation of relatively large amounts of certain alcohols.

In accordance with the present invention there is provided a pharmaceutical composition comprising as an active ingredient a therapeutically effective amount of a compound being a member selected from the group of racemic, S(−), and R(+)-N-propargyl-1-aminoindan or a pharmaceutically acceptable salt thereof, and at least 60% by weight of at least one alcohol being a member selected from the group of pentahydric and hexahydric alcohols.

In a preferred embodiment of the present invention the active ingredient is R(+)-N-propargyl-1-aminoindan.

Preferably the composition comprises at least 70% of said at least one alcohol.

Typically the alcohol used in accordance with of the invention, is a member selected from the group of mannitol, xylitol and sorbitol.

In accordance with the invention the PAI-comprising composition may further include citric acid, preferably in an amount of 0.5 to 2% by weight.

If desired, compositions according to the invention may further comprise magnesium stearate, preferably in an amount of 0.1 to 0.5% by weight. According to this embodiment, where the amount of said at least one alcohol is less than 70% by weight, the composition further comprises citric acid in an amount specified above. Where the amount of said at least one alcohol is at least 70% by weight, the inclusion of citric acid is optional.

The composition of the present invention may optionally also include conventional additives such as fillers, lubricants, disintegrants, glidants, flavoring agents, sweeteners, coloring agents, and the like, all as known per se. Examples of fillers which may be used in accordance with the present invention are lactose, starch, microcrystalline cellulose, maltrin and the like.

The compositions of the present invention may be prepared by methods known per se, familiar to those skilled in the art. For example, PAI and all other ingredients (with the exception of the lubricant, when used) may be screened and mixed thoroughly in a suitable granulating machine. The granulation may occur in the presence of purified water, following which the composition is dried. The dry granulate may then be milled, lubricated and compressed into tablets. R(+) PAI itself may be prepared, for example, according to the process described in Example 6B of WO95/11016.

The following non-limiting examples are given by way of illustration.

EXAMPLES

Example 1

|  | mg/tablet |
| --- | --- |
| R(+)-N-propargyl-1-aminoindan mesylate | 3.12 |
| Mannitol | 62.5 |
| Maltodextrin (Maltrin 150) | 36.0 |
| Croscarmellose sodium (Ac-Di-Sol) | 2.1 |
| Talc | 1.5 |

Example 2

|  | mg/tablet |
| --- | --- |
| R(+)-N-propargyl-1-aminoindan mesylate | 1.56 |
| Mannitol | 79.14 |
| Starch | 10.0 |
| Pregelatinized starch | 10.0 |
| Colloidal silicon dioxide | 0.6 |
| Talc | 2.0 |
| Stearic acid | 2.0 |

Example 3

|  | mg/tablet |
| --- | --- |
| R(+)-N-propargyl-1-aminoindan mesylate | 3.12 |
| Mannitol | 76.58 |
| Starch | 10.0 |
| Pregelatinized starch | 10.0 |
| Colloidal silicon dioxide | 0.6 |
| Citric acid | 1.0 |
| Talc | 2.0 |

Example 4

|                                           | mg/tablet |
|-------------------------------------------|-----------|
| R(+)-N-propargyl-1-aminoindan mesylate    | 3.12      |
| Mannitol                                  | 69.88     |
| Lactose (hydrous)                         | 14.0      |
| Starch                                    | 14.0      |
| Glyceryl Behenate (Compitrol 888 ATO)     | 2.0       |

Example 5

|                                                  | mg/tablet |
|--------------------------------------------------|-----------|
| R(+)-N-propargyl-1-aminoindan mesylate           | 3.12      |
| Mannitol                                         | 77.28     |
| Starch                                           | 10.0      |
| Starch STA-RX 1500                               | 10.0      |
| Colloidal silicon dioxide, Aerosil               | 0.6       |
| Hydrogenated vegetable type I (Sterotex Dritex)  | 2.0       |

Example 6

In order to compare the compositions of the present invention with those known in the prior art, two of the above formulations were compared with a formulation described in WO95/11016.

Formulation of WO95/11016 (Example 20)

|                                   | mg/tablet |
|-----------------------------------|-----------|
| R(+)-N-propargyl-1-aminoindan HCl | 1.56      |
| Lactose (hydrous)                 | 50.0      |
| Pregelatinized starch             | 36.0      |
| Microcrystalline cellulose        | 14.0      |
| Sodium starch glycolate           | 2.14      |
| Talc                              | 1.0       |
| Magnesium stearate                | 0.5       |

This formulation, as well as those described under Examples 2 and 3 of the present application were subjected to 6 months at 40° C. and 75% humidity. The percentage of degradants of the active material was assayed at the end of the six month period.

The following procedure was adopted to determine the degradation of the formulations prepared. The tablets were finely powdered and extracted with a diluent such as a mixture of water, acetonitrile and perchloric acid. An aliquot of the extraction product was injected into an HPLC and eluted using the same mixture as said diluent mixture. The area corresponding to the PAI compound was determined as was that of any other major peak. The calculations of degradation percent was made by comparing the areas of the measured peaks with those obtained from the standard preparation.

It was found that the formulation prepared according to the disclosure of Example 20 of WO95/11016 contained after storage 3.08% degradants whereas the formulations of Examples 2 and 3 contained 0.51% and less than 0.1% degradants, respectively.

Example 7

Formulations according to the present invention and others according to the description given in Example 20 of WO95/11016 were prepared containing the ingredients shown in Table 1. The formulations described in this Table are designated "PCT" when prepared in accordance with the disclosure in WO95/11016, or by a number which corresponds to the number of the Example in the present application, in which they are described. The qualifying symbols of A, B, C or D appearing next to some of these designations denote certain variations in said formulations. The percentage of degradation, presented in Table 2, was calculated for all the formulations of Table 1, after storing them for 1 month at 55° C. or for 6 months at 40° C. and 75% humidity. Those formulations stored according to the latter storing conditions are marked in the Table with an astrix (*). As can be seen from Table 2, the stabilities of all the compositions of the present invention was superior to those of the prior art.

TABLE 1

| Example No. | PCT mg | PCT-A mg | PCT-B mg | PCT-C mg | 1 mg | 1A mg | 1B mg | 1C mg | 1D mg | 2 mg | 2A mg | 3 mg | 3A mg | 4 mg | 5 mg | 5A mg | 5B mg | 5C mg | 8 mg | 9 mg |
|---|---|---|---|---|---|---|---|---|---|---|---|---|---|---|---|---|---|---|---|---|
| N-Propargyl-1(R)-Aminoindan Mesylate | 1.56 | 5.0 | 1.0 | 7.81 | 3.12 | 3.12 | 1.56 | 3.12 | 1.56 | 1.56 | 1.56 | 3.12 | 1.56 | 3.12 | 3.12 | 1.56 | 1.56 | 1.56 | 1.56 | 1.56 |
| Mannitol USP | | | | | 62.5 | 62.5 | | | | 79.14 | 78.44 | 76.58 | 77.44 | 69.88 | 77.28 | 78.87 | 78.87 | 78.87 | | |
| Starch STA-RX 1500 | 36.0 | 47.0 | 36.0 | 47.0 | | | 36.0 | 36.0 | 36.0 | 10.0 | 10.0 | 10.0 | 10.0 | | 10.0 | 10.0 | 10.0 | 10.0 | 10.0 | 10.0 |
| Starch NF | | | | | | | | | | | | | | 14.0 | | | | | 10.0 | 10.0 |
| Starch NF (in paste) | | | | | | | | | | 5.6 | 10.0 | 5.6 | | | | | | | | |
| | | | | | | | | | | 4.4 | | 4.4 | | | | | | | | |
| Colloidal Silicon Dioxide (Aerosil 200) | | | | | | | | | | 0.6 | 0.6 | 0.6 | 0.6 | 0.6 | 0.6 | 0.6 | 0.6 | 0.6 | 0.6 | 0.6 |
| Citric acid | | | | | | | | 1.0 | 2.0 | | | 1.0 | 1.0 | | | | | | | |
| Talc USP | 1.0 | 1.5 | 1.0 | 1.5 | 1.5 | 1.5 | 1.0 | 1.0 | 1.0 | 2.0 | 2.0 | 2.0 | 2.0 | | | 2.0 | 2.0 | 2.0 | 2.0 | 2.0 |
| Microcrystalline Cellulose (Avicel 102) | 14.0 | 20.0 | 14.0 | 20.0 | | | 14.0 | 14.0 | 14.0 | | | | | | | | | | | |
| Stearic acid NF | | | | | | | 2.0 | | | 2.0 | 2.0 | 2.0 | 2.0 | | | 2.0 | | | | |
| Lactose NF Hydrous | 50.0 | 66.0 | 50.0 | 66.0 | | | 50.0 | 47.44 | 46.44 | | | | | 14.0 | | | | | | |
| Sodium Starch Glycolate | 2.14 | 3.0 | 2.2 | 2.99 | | | 2.14 | 2.14 | 2.14 | | | | | | | | | | | |
| Magnesium Stearate | 0.5 | 0.7 | 0.5 | 0.7 | | 0.52 | 0.1 | 0.5 | 0.5 | | | | | | | 0.1 | 0.5 | 0.5 | | |
| AC-DI-SOL | | | | | 2.1 | 2.1 | | | | | | | | | | | | | | |
| Lactose spray dried | | | | | 36.0 | 36.0 | | | | | | | | | | | | | | |
| Compritol 888 ATO | | | | | | | | | | | | | | 2.0 | | | | | | |
| Maltrin | | | | | | | | | | | | | | | | | | | | |
| Sorbitol Xilitato 300 | | | | | | | | | | | | | | | | | | | 78.84 | 78.84 |
| Sterotex - Dritex | | | | | | | | | | | | | | | 2.0 | | | | | |
| Total Weight (mg) | 105.2 | 143.2 | 104.7 | 146.0 | 105.22 | 105.74 | 106.8 | 105.2 | 105.2 | 105.3 | 104.6 | 105.3 | 104.6 | 103.0 | 103.0 | 105.13 | 103.53 | 105.53 | 105.0 | 105.0 |

TABLE 2

| Example No: | % Degradants | Mannitol (%) | Sorbitol (%) | Xylitol (%) | Magneisum stearate (%) | Citric acid (%) |
|---|---|---|---|---|---|---|
| PCT(*) | 2.26 | — | | | 0.5 | — |
| PCT-A | 2.76 | — | | | 0.49 | — |
| PCT-B | 1.46 | — | | | 0.49 | — |
| PCT-C(*) | 2.59 | — | | | 0.5 | — |
| 1 | 1.22 | 59.4 | | | — | — |
| 1A | 3.97 | 59.1 | | | 0.49 | — |
| 1B | 2.04 | — | | | 0.1 | — |
| 1C | 1.04 | — | | | 0.47 | 0.95 |
| 1D | 0.40 | — | | | 0.47 | 1.9 |
| 2 | 0.29 | 75.1 | | | — | — |
| 2A | 0.27 | 75 | | | | |
| 3 | 0.02 | 72.7 | | | — | 0.95 |
| 3A | 0.02 | 74 | | | | 0.95 |
| 4 | 0.02 | 67.8 | | | — | — |
| 5 | 0.21 | 75 | | | — | — |
| 5A | 0.32 | 75 | | | 0.1 | — |
| 5B | 0.65 | 76.2 | | | 0.47 | — |
| 5C | 0.52 | 74.7 | | | 0.47 | — |
| 6 | 0.74 | | 75.1 | | — | — |
| 7 | 1.01 | | | 75.1 | — | — |

What is claimed is:

1. A pharmaceutical composition in tablet form comprising as an active ingredient a therapeutically effective amount of R(+)-N-propargyl-1-aminoindan or a pharmaceutically acceptable salt thereof, and at least one alcohol selected from the group consisting of pentahydric and hexahydric alcohols.

2. The pharmaceutical composition of claim 1, wherein said at least one alcohol comprises at least 60% by weight of the total composition.

3. The pharmaceutical composition of claim 1, wherein the alcohol is selected from the group consisting of mannitol, xylitol and sorbitol.

4. The pharmaceutical composition of claim 1, further comprising citric acid.

5. The pharmaceutical composition of claim 4, wherein the amount of citric acid is 0.5 to 2% by weight of the total composition.

6. The pharmaceutical composition of claim 1, further comprising magnesium stearate.

7. The pharmaceutical composition of claim 5, wherein the amount of magnesium stearate is 0.1 to 0.5% by weight of the total composition.

8. The pharmaceutical composition of claim 1, in which the amount of said at least one alcohol is between 60% and 70% of the total composition, and further comprising citric acid.

9. The pharmaceutical composition of claim 1, wherein said active ingredient is R(+)-N-propargyl-1-aminoindan.

10. A pharmaceutical composition in tablet form comprising as an active ingredient a therapeutically effective amount of R(+)-N-propargyl-1-aminoindan or a pharmaceutically acceptable salt thereof, and at least 75% by weight of at least one alcohol selected from the group consisting of mannitol, xylitol and sorbitol.

11. The pharmaceutical composition of claim 10, wherein the amount of R(+)-N-propargyl-1-aminoindan or a pharmaceutically acceptable salt thereof is 3.0% or less by weight of the composition, and wherein the alcohol at least 75% by weight of the composition.

12. The pharmaceutical composition of claims, wherein the alcohol is mannitol.

13. A pharmaceutical composition comprising as an active ingredient a therapeutically effective amount of R(+)-N-propargyl-1-aminoindan or a pharmaceutically acceptable salt thereof, and at least one alcohol selected from the group consisting of pentahydric and hexahydric alcohols.

14. The pharmaceutical composition of claim 13, wherein said at least one alcohol comprises at least 60% by weight of the total composition.

15. The pharmaceutical composition of claim 13, wherein, the alcohol is selected from the group consisting of mannitol, xylitol and sorbitol.

16. The pharmaceutical composition of claim 13, further comprising citric acid.

17. The pharmaceutical composition of claim 16, wherein the amount of citric acid is 0.5 to 2% by weight of the total composition.

18. The pharmaceutical composition of claim 13, further comprising magnesium stearate.

19. The pharmaceutical composition of claim 18, wherein the amount of magnesium stearate is 0.1 to 0.5% by weight of the total composition.

20. The pharmaceutical composition of claim 13, in which the amount of said at least one alcohol is between 60% and 70% of the total composition, and further comprising citric acid.

21. The pharmaceutical composition of claim 13, wherein said active ingredient is R(+)-N-propargyl-1-aminoindan.

22. A pharmaceutical composition comprising as an active ingredient a therapeutically effective amount of R(+)-N-propargyl-1-aminoindan or a pharmaceutically acceptable salt thereof, and at least 75% by weight of at least one alcohol selected from the group consisting of mannitol, xylitol and sorbitol.

23. The pharmaceutical composition of claim 22, wherein the amount of R(+)-N-propargyl-1-aminoindan or a pharmaceutically acceptable salt thereof is 3.0% or less by weight of the composition, and wherein the alcohol at least 75% by weight of the composition.

24. The pharmaceutical composition of claim 23, wherein the alcohol is mannitol.

25. The pharmaceutical composition of claim 2, wherein the amount of R(+)-N-propargyl-1-aminoindan or a pharmaceutically acceptable salt thereof is 3.0% or less by weight of the composition.

26. The pharmaceutical composition of claim 14, wherein the amount of R(+)-N-propargyl-1-aminoindan or a pharmaceutically acceptable salt thereof is 3.0% or less by weight of the composition.

* * * * *

UNITED STATES PATENT AND TRADEMARK OFFICE
CERTIFICATE OF CORRECTION

PATENT NO. : 6,126,968
APPLICATION NO. : 09/043475
DATED : October 3, 2000
INVENTOR(S) : Tirtsah Berger Peskin and Fanny Caciularu It is certified that error appears in the above-identified patent and that said Letters Patent is hereby corrected as shown below:

Col. 7, in Claim 12, "The pharmaceutical composition of claims" should read -- The pharmaceutical composition of claim 11 --

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

PATENT NO.          : 6,126,968
APPLICATION NO. : 09/043475
DATED                  : October 3, 2000
INVENTOR(S)         : Tirtsah Berger Peskin and Fanny Caciularu It is certified that error appears in the above-identified patent and that said Letters Patent is hereby corrected as shown below:

Col. 7, in Claim 12, line 61, "The pharmaceutical composition of claims" should read -- The pharmaceutical composition of claim 11 --

This certificate supersedes the Certificate of Correction issued October 13, 2009.

Signed and Sealed this

Seventeenth Day of November, 2009

David J. Kappos
*Director of the United States Patent and Trademark Office*